United States Patent
Lu et al.

(10) Patent No.: US 11,375,942 B2
(45) Date of Patent: Jul. 5, 2022

(54) METHOD FOR EXTRACTING F WAVE FROM SINGLE-LEAD ELECTROCARDIOGRAPHY SIGNAL

(71) Applicant: Guangdong University of Technology, Guangzhou (CN)

(72) Inventors: Jun Lu, Guangzhou (CN); Lei Li, Meizhou (CN); Shengli Xie, Guangzhou (CN); Jie Luo, Dongguan (CN); Zongze Wu, Guangzhou (CN); Qiyu Yang, Guangzhou (CN); Sihai Qiu, Shenzhen (CN); Binbin Yan, Shenzhen (CN); Dewei Chen, Shenzhen (CN)

(73) Assignee: GUANGDONG UNIVERSITY OF TECHNOLOGY, Guangzhou (CN)

(*) Notice: Subject to any disclaimer, the term of this patent is extended or adjusted under 35 U.S.C. 154(b) by 0 days.

(21) Appl. No.: 17/497,052

(22) Filed: Oct. 8, 2021

(65) Prior Publication Data

US 2022/0110576 A1   Apr. 14, 2022

(30) Foreign Application Priority Data

Oct. 9, 2020 (CN) .......................... 202011072556.3

(51) Int. Cl.
*A61B 5/00* (2006.01)
*A61B 5/366* (2021.01)
*G16H 50/30* (2018.01)
*G06N 3/04* (2006.01)

(52) U.S. Cl.
CPC .............. *A61B 5/366* (2021.01); *G06N 3/049* (2013.01); *G16H 50/30* (2018.01)

(58) Field of Classification Search
CPC ........ A61B 5/366; A61B 5/7264; A61B 5/361; A61B 5/7267; A61B 5/318; A61B 5/349; A61B 5/352; A61B 5/7235
See application file for complete search history.

(56) References Cited

U.S. PATENT DOCUMENTS

2008/0167567 A1* 7/2008 Bashour .................. A61B 5/361
                                                600/518
2020/0352461 A1* 11/2020 Banerjee .............. G06N 3/0454

OTHER PUBLICATIONS

Mousavi et al. "ECGNET: Learning Where to Attend for Detection of Atrial Fibrillation with Deep Visual Attention", School of Informatics, Computing and Cyber Systems, Northern Arizona University, Flagstaff, USA (Year: 2019).*

* cited by examiner

*Primary Examiner* — Rex R Holmes
*Assistant Examiner* — Sana Sahand
(74) *Attorney, Agent, or Firm* — WPAT, PC

(57) ABSTRACT

A method for extracting f wave from a single-lead electrocardiography signal is provided. The method includes: establishing a two-channel temporal convolutional neural network model, including two coding submodules, two mask estimation submodules, an information fusion module and two decoding submodules; constructing a training data set of ECG signals; training the two-channel temporal convolutional neural network model, and saving the trained model. The two-channel temporal convolution neural network encodes and decodes a QRST complex and the f wave respectively, and uses a mask of information fusion to estimate and construct regular items to restrict a distribution difference of QRST component coding features, so as to reduce the distortion of the QRST complex, select potential features of a QRST complex and f wave with high signal-to-noise ratio, and thus improve a detection accuracy of the f wave.

9 Claims, 1 Drawing Sheet

METHOD FOR EXTRACTING F WAVE FROM SINGLE-LEAD ELECTROCARDIOGRAPHY SIGNAL

TECHNICAL FIELD

The invention relates to the field of signal processing, in particular to a method for extracting f wave from a single-lead electrocardiography (ECG) signal.

BACKGROUND

Atrial fibrillation is the most common supraventricular arrhythmia. The risk of stroke in patients with atrial fibrillation is four to five times higher than that in people who are not affected by atrial fibrillation. Among patients with heart disease, the mortality rate of atrial fibrillation is twice that of other patients. When atrial fibrillation occurs, P wave is replaced by f wave with rapid vibration as well as different amplitude and shape, which causes irregular and frequently changing ventricular electrical activity. The physical parameters of f wave (such as amplitude and frequency spectrum) are often used for clinical diagnosis of atrial fibrillation, which is of great significance to the study of electrophysiological activity mechanism of atrial fibrillation.

The QRST wave of ventricular activity and f wave of atrial activity are overlapped in both time domain and frequency domain, which restricts the detection accuracy of f wave. To solve this problem, researchers have proposed many methods to extract f wave, which can be roughly divided into two types: multi-lead and single-lead. Multi-lead method adopts blind source signal separation, spatio-temporal elimination and other technologies, and uses the correlation between multi-lead electrocardiogram signals to separate QRST complex and f wave. Although this method has a good effect on f wave detection, it needs to arrange multiple electrodes, which is not convenient for mobile ECG equipment. Single-lead method often uses techniques such as average template elimination and Bayesian filtering to eliminate QRST components or estimate parameters of f wave according to prior model, so as to extract f wave. Although the method of single lead is convenient for mobile ECG monitoring, it is sensitive to abnormal beats (such as the morphological changes of beats caused by premature ventricular beats) and has low detection accuracy.

The traditional multi-lead f wave extraction method uses the correlation between ECG signals in each lead to suppress QRST components. This kind of method needs to attach multiple electrode patches to the patient, which limits the patient's actions and is not conducive to long-term monitoring and dynamic detection. According to the quasi-periodicity of ECG signal, the single-lead f wave extraction method constructs QRST template for matched filtering to extract f wave. However, QRST waveform distortion and abnormal heart beat interval seriously affect the accuracy of QRST template estimation, thus affecting the accuracy of f wave extraction.

SUMMARY

An objective of the invention is to provide a method for extracting f wave based on a two-channel temporal convolutional network, so as to improve a detection accuracy of the f wave and provide reliable basis for clinical diagnosis of atrial fibrillation.

In order to achieve the above objective, the invention adopts the following technical scheme.

Specifically, the method for extracting f wave from a single-lead ECG signal is provided and includes the follow steps:

establishing a two-channel temporal convolutional neural network model, where the two-channel temporal convolutional neural network model includes two coding submodules, two mask estimation submodules, an information fusion module and two decoding submodules, where the two coding submodules are respectively used for extracting a coding feature vector of ventricular QRST complex and a coding feature vector of the f wave; the two mask estimation submodules are respectively used for extracting a potential feature vector of the f wave and a potential feature vector of the ventricular QRST complex according to the coding feature vector of the ventricular QRST complex and the coding feature vector of the f wave; the information fusion module is used for performing feature fusion on the potential feature vector of the f wave and the potential feature vector of the ventricular QRST complex in the coding space, to estimate a mask feature vector of the ventricular QRST complex and a mask feature vector of the f wave; the two decoding submodules are respectively used for reconstructing a time domain signal of the ventricular QRST complex and a time domain signal of the f wave according to a weighted result of the mask feature vector and the coding feature vector of the ventricular QRST complex and a weighted result of the mask feature vector and the coding feature vector of the f wave;

constructing a training data set of ECG signals, training the two-channel temporal convolutional neural network model according to the training data set of ECG signals to obtain a trained model, and saving the trained model; and inputting an unknown mixed ECG signal into the trained model, to extract the time domain signal of the f wave.

In an embodiment, the two-channel temporal convolutional neural network model is established based on a probability graph model, and a probability factorization formula of the probability graph model is expressed as follows:

$$P(x_{VA}, x_{AA} | x) = \int_x P(x_{VA} | \tilde{Z}_{VA}) P(x_{AA} | \tilde{Z}_{AA}) P(\tilde{Z}_{VA} | M_{VA}, Z_{VA}) \cdot$$
$$P(\tilde{Z}_{AA} | M_{AA}, Z_{AA}) P(M_{VA} | F_{VA}, F_{AA}) P(M_{AA} | F_{VA}, F_{AA}) \cdot$$
$$P(F_{VA} | Z_{VA}) P(F_{AA} | Z_{AA}) P(Z_{VA} | x) P(Z_{AA} | x) dx$$

Specifically, $P(x_{VA}, x_{AA}|x)$ represents a conditional distribution probability, x represents a measured mixed ECG signal, $x_{VA}$ represents the time domain signal of the ventricular QRST complex, $x_{AA}$ represents the time domain signal of the f wave, $Z_{VA}$ and $Z_{AA}$ represent coding feature vectors of the ventricular QRST complex and the f wave, $F_{AA}$ and $F_{VA}$ represent the potential feature vectors of the QRST complex and the f wave, $M_{VA}$ and $M_{AA}$ represent the mask feature vectors of the QRST complex and the f wave, $\tilde{Z}_{VA}$ and $\tilde{Z}_{AA}$ represent weighted feature vectors, and P( ) represents a probability.

In an embodiment, the constructing the training data set of the ECG signals includes:

constructing the training data set $D_{tr} = \{x^i, x_{VA}^i, x_{AA}^i\}_{i=1}^{n_{tr}}$ using a ECG signal data set marked with a QRST complex position and an f wave position, where $n_{tr}$ represents a total number of ECG records in the training data set, $x^i \in R^{1 \times T}$ represents the i-th ECG record of the ECG records, T represents the number of time sampling points, $x_{VA}^i \in R^{1 \times T}$ represents a clean QRST complex position label in the i-th ECG record, and $x_{AA}^i \in R^{1 \times T}$ represents a clean f wave position label in the i-th ECG record.

In an embodiment, for each of the two coding submodules, a one-dimensional convolutional neural network is configured for coding, and the process of extracting the features of the ventricular QRST complex and the features of the f wave respectively by the two coding submodules, includes:

dividing each ECG record into K ECG segments each of a fixed length L, recorded as: $X \in R^{K \times L}$; inputting respectively X into the one-dimensional convolutional networks for the two coding submodules, to extract coding feature vectors of the ventricular QRST complex and the f wave, respectively recorded as $Z_{VA}$ and $Z_{AA} \in R^{K \times N}$, where N is the number of coding bases, and the coding feature vectors of the ventricular QRST complex and the f wave are calculated as follows:

$$\begin{cases} Z_{VA} = X B_{VA} \\ Z_{AA} = X B_{AA} \end{cases}$$

where $B_{VA}$ and $B_{AA} \in R^{L \times N}$ represent coding basis vectors.

In an embodiment, the process of extracting the potential feature vector of the f wave and the potential feature vector of the ventricular QRST complex according to the coding feature vector of the ventricular QRST complex and the coding feature vector of the f wave by the two mask estimation submodules, includes:

inputting the coding feature vectors $Z_{VA}$ and $Z_{AA}$ respectively into two mask estimation submodules, to obtain the potential feature vectors of the f wave and the ventricular QRST complex, recorded as $F_{AA}$, $F_{VA} \in R^{K \times N}$ where each of the two mask estimation submodules contains a temporal convolutional network (TCN).

In an embodiment, the process of performing by the information fusion module the feature fusion on the potential feature vector of the f wave and the potential feature vector of the ventricular QRST complex in the coding space to estimate the mask feature vector of the ventricular QRST complex and the mask feature vector of the f wave, includes:

concatenating the potential feature vectors $F_{AA}$ and $F_{VA}$ in the coding space, to obtain a concatenated feature vector $F_{concat} = [F_{VA}, F_{AA}] \in R^{K \times 2N}$; and inputting the concatenated feature vector into a one-dimensional convolution network, to estimate the mask feature vectors of the ventricular QRST complex and the f wave, respectively recorded as $M_{VA}$, $M_{AA} \in R^{K \times N}$.

In an embodiment, obtaining the weighted result of the mask feature vector and the coding feature vector of the ventricular QRST complex and the weighted result of the mask feature vector and the coding feature vector of the f wave includes:

weighting the mask feature vectors $M_{VA}$ and $M_{AA}$ output by the two mask estimation submodules respectively using the coding feature vectors $Z_{VA}$ and $Z_{AA}$, to obtain weighted feature vectors of the ventricular QRST complex and the f wave, respectively recorded as $\tilde{Z}_{VA} \tilde{Z}_{AA} \in R^{K \times N}$ where the weighted feature vectors of the ventricular QRST complex and the f wave are calculated as follows:

$$\begin{cases} \tilde{Z}_{VA} = M_{VA} \odot Z_{VA} \\ \tilde{Z}_{AA} = M_{AA} \odot Z_{AA} \end{cases}$$

where $\odot$ indicates dot product of elements.

In an embodiment, the process of two decoding submodules reconstructing by the two decoding submodules the time domain signal of the ventricular QRST complex and the time domain signal of the f wave includes:

inputting individually the weighted feature vectors $\tilde{Z}_{VA}$ and $\tilde{Z}_{AA}$ into a one-dimensional deconvolution network, to reconstruct the time domain signal of the ventricular QRST complex recorded as $\tilde{X}_{VA} \in R^{K \times L}$, and the time domain signal of the f wave recorded as $\tilde{X}_{AA} \in R^{K \times L}$, where the time domain signal of the ventricular QRST complex and the time domain signal of the f wave are calculated as follows:

$$\begin{cases} \tilde{X}_{VA} = \tilde{Z}_{VA} D_{VA} \\ \tilde{X}_{AA} = \tilde{Z}_{AA} D_{AA} \end{cases}$$

where $D_{VA}$, $D_{AA} \in R^{N \times L}$ represent the decoding basis vectors;

connecting K pieces of reconstructed fragments each of a length L in $\tilde{X}_{VA}$ and $\tilde{X}_{AA}$ in series in turn, and estimating the time domain signals of the QRST complex and the f wave, recorded as $\tilde{x}_{VA}$, $\tilde{x}_{AA} \in R^{1 \times T}$.

In an embodiment, the two-channel temporal convolutional neural network model is trained using an objective function, expressed as follows:

$$\min J(\omega) = -\sum_{i=1}^{n_{tr}} SNR_{AA}^i - \alpha \cdot \sum_{i=1}^{n_{tr}} SNR_{VA}^i + \beta \cdot S_{VA}$$

where $\omega$ represents all trainable parameters of the two-channel temporal convolutional neural network model, $\alpha$ and $\beta$ represents compromise coefficients, $SNR_{VA}$ and $SNR_{AA}$ respectively represent a signal-to-noise ratio of the ventricular QRST complex and a signal-to-noise ratio of the f wave estimated by the model, $S_{VA}$ represents a sum of distances between the coding feature vectors of ventricular QRST complexes of every two of ECG samples, i represents a number of the i-th sample of the ECG samples, and $n_{tr}$ represents a total number of ECG records in the training data set.

In another aspect, a computer is provided, which includes a processor, a memory and a computer program stored in the memory, and when the computer program is executed by the processor, the steps of realizing the f wave extraction method of the single-lead ECG signal are realized.

In yet another aspect, a non-transitory computer readable storage medium is provided, which stores a computer program, and when the computer program is executed by a processor, the steps of realizing the f wave extraction method of the single-lead ECG signal are realized.

Compared with the previous technology, the invention has the following technical advantages:

1. The two-channel temporal convolution neural network provided by the invention encodes and decodes QRST complex and f wave respectively, estimates and constructs regular items by using masks of information fusion to restrict the distribution difference of QRST component coding features, reduces the distortion of QRST complex, and selects QRST complex and f wave potential features with high signal-to-noise ratio, thereby improving the f wave detection accuracy. In this invention, the method that constrains the distribution difference of QRST component coding features is named DT-FENet, and the method without constraining the distribution difference is named DT-FENet w/o constrain.

2. Simulation and experimental results show that compared with the diffusion distance non-local euclidean median (DD-NLEM) and the extended Kalman smoother (EKS), the f wave extracted by this method has higher accuracy.

DETAILED DESCRIPTION OF THE EMBODIMENTS

Figure 1:
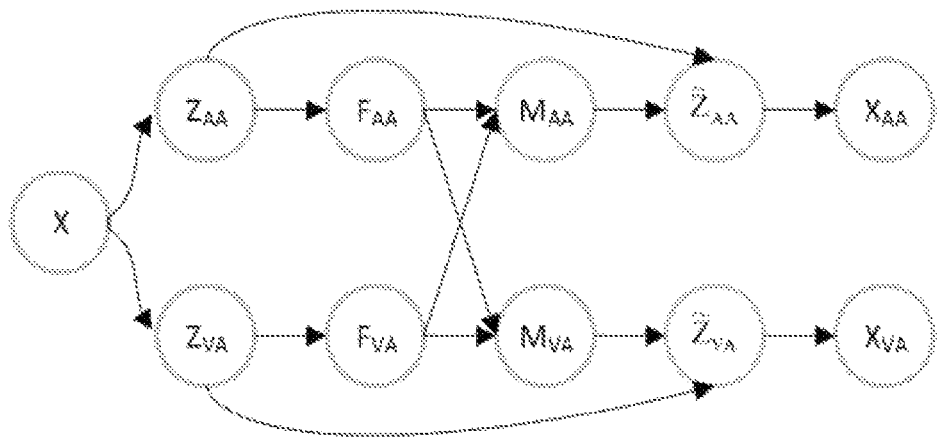
FIG. 1 shows a probability diagram model.

With reference to FIG. 1, the invention provides a method for extracting f wave from a single-lead ECG signal. The invention proposes a probability diagram model based on a design of a coding and decoding structure (as shown in FIG. 1), and constructs an attention mechanism to improve signal-to-noise ratios of potential feature vectors of ventricular QRST complex and the f wave, so that a measured ECG signal x can more clearly separate a time domain signal $x_{VA}$ of the ventricular QRST complex and a time domain signal $x_{AA}$ of the f wave. As shown in FIG. 1, a conditional distribution $P(x_{VA}, x_{AA}|x)$ can be decomposed into:

$$P(x_{VA}, x_{AA} | x) = \qquad \text{Formula 1}$$
$$\int_x P(x_{VA} | \tilde{Z}_{VA}) P(x_{AA} | \tilde{Z}_{AA}) P(\tilde{Z}_{VA} | M_{VA}, Z_{VA}) \cdot$$
$$P(\tilde{Z}_{AA} | M_{AA}, Z_{AA}) P(M_{VA} | F_{VA}, F_{AA}) P(M_{AA} | F_{VA}, F_{AA}) \cdot$$
$$P(F_{VA} | Z_{VA}) P(F_{AA} | Z_{AA}) P(Z_{VA} | x) P(Z_{AA} | x) dx.$$

In the above probability factorization formula, $Z_{VA}$ and $Z_{AA}$ represent coding feature vectors of the QRST complex and the f wave, $F_{AA}$ and $F_{VA}$ represent potential feature vectors of the QRST complex and the f wave, $M_{VA}$ and $M_{AA}$ represent mask feature vectors of the QRST complex and the f wave, $\tilde{Z}_{VA}$ and $\tilde{Z}_{AA}$ represent weighted feature vectors, and P( ) represents a probability.

As shown in FIG. 1, the probability map model with self-attention mechanism is designed based on the coding and decoding structure. An upper channel decodes atrial activity signals (e.g., f wave), while a lower channel decodes ventricular activity signals (QRST complex), and captures relevant information between channels through information interaction of self-attention mask, so that the upper channel pays more attention to the features of the f wave and the lower channel pays more attention to the feature extraction of the QRST complex. Finally, the QRST complex and the f wave are generated by decoder.

In the invention, the method for extracting f wave from the single-lead ECG signal may include steps 1 to 4.

In step 1, firstly, a training data set $D_{tr}=\{x^i, x_{VA}^i, x_{AA}^i\}_{i=1}^{n_{tr}}$ is constructed by using a ECG signal data set marked with a QRST complex position and an f wave position, where $n_{tr}$ represents a total number of ECG records in the training data set, $x^i \in R^{1 \times T}$ represents the i-th ECG record of the ECG records, T represents the number of time sampling points, $x_{VA}^i \in R^{1 \times T}$ represents a clean QRST complex position label in the i-th ECG record, and $x_{AA}^i \in R^{1 \times T}$ represents a clean f-wave position label in the i-th ECG record.

Figure 2:
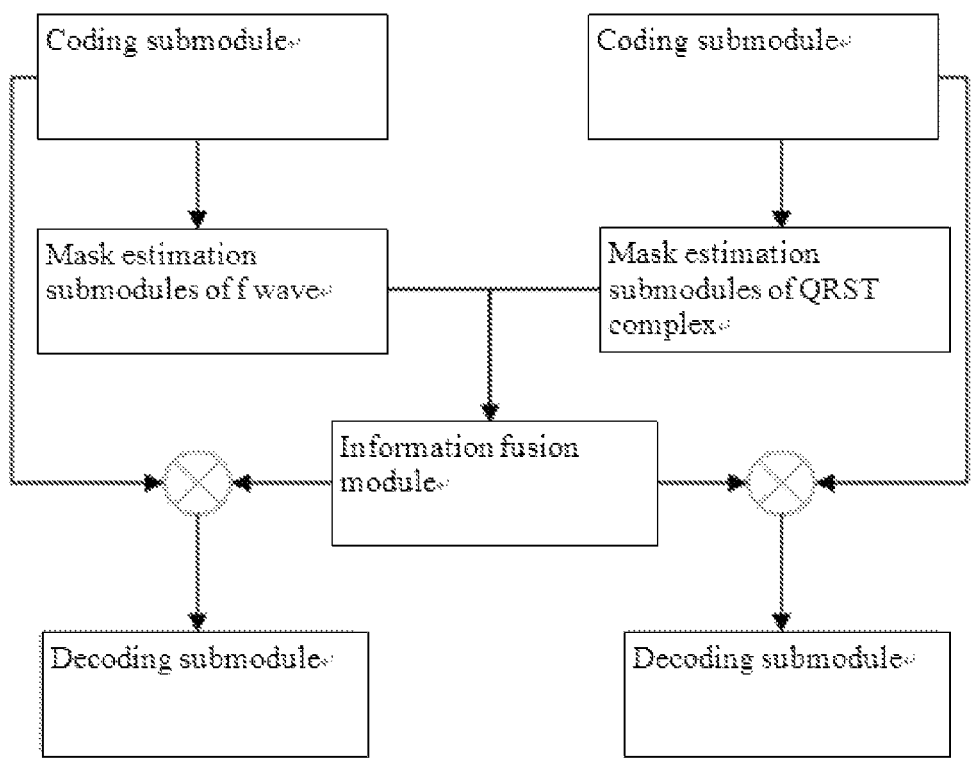
FIG. 2 shows a two-channel temporal convolutional neural network model.

In step 2, based on the probability factorization formula of the probability graph model, a two-channel temporal convolutional neural network model is established, as shown in FIG. 2, which is used to extract the f wave; the model includes two coding submodules, two mask estimation submodules, an information fusion module and two decoding submodules. For example, the above submodules are software modules, which are stored in a memory and executable by a processor coupled to the memory.

Specifically, the two coding submodules are respectively used for extracting a coding feature vector of the ventricular QRST complex and a coding feature vector of the f wave;

the two mask estimation submodules are respectively used for extracting a potential feature vector of the f wave and a potential feature vector of the ventricular QRST complex according to the coding feature vector of the ventricular QRST complex and the coding feature vector of the f wave;

the information fusion module is used for performing feature fusion on the potential feature vector of the f wave and the potential feature vector of the ventricular QRST complex in the coding space, to estimate a mask feature vector of the ventricular QRST complex and a mask feature vector of the f wave; and the two decoding submodules are respectively used for reconstructing a time domain signal of the ventricular QRST complex and a time domain signal of the f wave according to the weighted results of the mask feature vector and the coding feature vector of the ventricular QRST complex and the weighted results of the mask feature vector and the coding feature vector of the f wave.

Next, with reference to FIG. 2, a specific processing process of each module of the two-channel temporal convolutional neural network model will be further explained, which includes steps 2.1, 2.2, 2.3, 2.4 and 2.5.

In step 2.1, the coding feature vectors of the ventricular QRST complex and the f wave are extracted by using the two coding submodules; and $P(Z_{VA}|x)$ and $P(Z_{AA}|x)$ are parameterized by using the coding submodule. In the invention, one-dimensional convolutional neural network is used for coding, and each ECG record is divided into k ECG segments each of a fixed length L, recorded as: $X \in R^{K \times L}$, and x is input into the one-dimensional convolutional network in the two coding submodules respectively in order to learn the transform domain; and thus the coding feature vectors of the ventricular QRST complex and the f wave are extracted and recorded as $Z_{VA}$, $Z_{AA} \in R^{K \times N}$ (N is the number of coding bases), and the specific calculation method is as follows:

$$\begin{cases} Z_{VA} = XB_{VA} \\ Z_{AA} = XB_{AA} \end{cases} \qquad \text{Formula 2}$$

where $B_{VA}$ and $B_{AA} \in R^{L \times N}$ are coding basis vectors.

In step 2.2, two mask estimation submodules are used to extract the potential feature vectors of the f wave and the ventricular QRST complex respectively according to the coding feature vectors of the ventricular QRST complex and the f wave.

Each of the mask estimation submodule is used to parameterize $P(F_{VA}|Z_{VA})$ and $P(F_{AA}|Z_{AA})$. In the invention, a temporary convolutional network (TCN) is used for mask estimation. The coding feature vectors $Z_{VA}$ and $Z_{AA}$ are respectively input into the two mask estimation submodule each containing the TCN, such as a mask estimation submodule of f wave and a mask estimation submodule of QRST complex in FIG. 2, and the potential feature vectors of the f wave and the ventricular QRST complex are obtained, recorded as $F_{AA}$, $F_{VA} \in R^{K \times N}$.

In step 2.3, according to the potential feature vector of the f wave and the potential feature vector of the ventricular QRST complex, feature fusion is performed by using the information fusion module, thereby estimating the mask feature vector of the ventricular QRST complex and the mask feature vector of the f wave.

$P(M_{VA}|F_{AA}, F_{VA})$ and $P(M_{AA}|F_{AA}, F_{VA})$ are parameterized using the information fusion module. In the invention, information fusion uses a concatenation and a one-dimensional convolutional neural network. In the coding space, the potential feature vectors $F_{AA}$ and $F_{VA}$ are concatenated to obtain a concatenated feature vector $F_{concat} = [F_{VA}, F_{AA}] \in R^{K \times 2N}$, and the concatenated feature vector is input to a one-dimensional convolution network, and then the mask features vectors of the ventricular QRST complex and the f wave are estimated, recorded as $M_{VA}, M_{AA} \in R^{K \times N}$.

In step 2.4, the mask feature vector and the coding feature vector of the ventricular QRST complex are weighted and the mask feature vector and the coding feature vector of the f wave are weighted.

The mask feature vectors $M_{VA}$ and $M_{AA}$ output by the two mask estimation submodules are used to weight the coding feature vectors $Z_{VA}$ and $Z_{AA}$, and the weighted feature vectors of the QRST complex and the f wave are respectively recorded as $\tilde{Z}_{VA}, \tilde{Z}_{AA} \in R^{K \times N}$, the specific calculation methods is as follows:

$$\begin{cases} \tilde{Z}_{VA} = M_{VA} \odot Z_{VA} \\ \tilde{Z}_{AA} = M_{AA} \odot Z_{AA} \end{cases} \quad \text{Formula 3}$$

where $\odot$ represents dot product of elements.

In step 2.5, the time domain signals of the ventricular QRST complex and the f wave are reconstructed by the two decoding submodules according to the weighted result of the mask feature vector and the coding feature vector of the ventricular QRST complex and the weighted result of the mask feature vector and the coding feature vector of the f wave.

Functions $P(\tilde{x}_{VA}|\tilde{Z}_{VA})$ and $P(\tilde{x}_{AA}|\tilde{Z}_{AA})$ are parameterized by the two decoding submodules. In the invention, a one-dimensional deconvolution neural network is used for decoding. The weighted feature vectors $\tilde{Z}_{VA}$ and $\tilde{Z}_{AA}$ are individually input into the one-dimensional deconvolution network, and the time domain signal of the ventricular QRST complex is reconstructed, recorded as $\tilde{X}_{VA} \in R^{K \times L}$ and the time domain signal of the f wave, recorded as $\tilde{X}_{AA} \in R^{K \times L}$, with the specific calculation formula as follows:

$$\begin{cases} \tilde{X}_{VA} = \tilde{Z}_{VA} D_{VA} \\ \tilde{X}_{AA} = \tilde{Z}_{AA} D_{AA} \end{cases} \quad \text{Formula 4}$$

where $D_{VA}, D_{AA} \in R^{N \times L}$ represent decoding basis vector. At last, K pieces of reconstructed fragments each of a length L in $\tilde{X}_{VA}$ and $\tilde{X}_{AA}$ are connected in series in turn, and finally two complete time domain signals of the QRST complex and the f wave are estimated, which are recorded as $\tilde{x}_{VA}, \tilde{x}_{AA} \in R^{1 \times T}$.

In step 3, the two-channel temporal convolutional neural network model is trained by using the training data set to obtain a trained model, and the trained model is saved for extracting the f wave from the ECG signal.

In this step, an objective function for the model training is:

$$\min J(\omega) = -\sum_{i=1}^{n_{tr}} SNR_{AA}^i - \alpha \cdot \sum_{i=1}^{n_{tr}} SNR_{VA}^i + \beta \cdot S_{VA} \quad \text{Formula 5}$$

where $\omega$ represents all trainable parameters of the model. $\alpha$, $\beta$ represent compromise coefficients, $SNR_{VA}$ and $SNR_{AA}$ respectively represent a signal-to-noise ratio of the ventricular QRST complex and a signal-to-noise ratio of the f wave estimated by the model, recorded as $$SNR_{VA}^i = 10 \log_{10} \frac{\|x_{VA}^i\|_2^2}{\|\tilde{x}_{VA}^i - x_{AA}^i\|_2^2} \text{ and}$$

$$SNR_{AA}^i = 10 \log_{10} \frac{\|x_{AA}^i\|_2^2}{\|\tilde{x}_{AA}^i - x_{AA}^i\|_2^2},$$

$\tilde{x}_{AA}^i$ and $x_{AA}^i$ respectively represent the an f wave and a clean f wave estimated by the model, $\tilde{x}_{VA}^i$ and $x_{VA}^i$ respectively represent a model estimated QRST complex and a clean QRST complex position tag in the i-th ECG record. $S_{VA}$ represents a sum of distances between the coding feature vectors of ventricular QRST complexes of every two of ECG samples, recorded as $$S_{VA} = \sum_{i,j=1}^{n_{tr}} \|p_{VA}^i - p_{VA}^j\|_2^2,$$

i and j respectively represent numbers of the i-th and j-th sample, and $p_{VA} \in R^{1 \times N}$ represents the coding feature vector of the ventricular QRST complex.

In the training process, an adam optimizer is selected as an optimizer. An initial gradient descent step is set to $1 \times 10^{-3}$. If an accuracy of the f wave extracted from three epochs appear continuously, a step size of gradient descent will be halved. In this embodiment, the model trains 80 epochs.

In step 4, an unknown mixed ECG signal is inputted into the trained model, thereby extracting time domain signals of the ventricular QRST complex and the f wave.

In an embodiment of the invention, a simulated f wave is provided by R. Alcaraz et al. in the paper Reference database and performance evaluation of methods for extraction of atrial fibrillatory waves in the ECG. The accuracy of atrial fibrillation signals extracted by simulation is expressed by Normalized mean square error (NMSE), which is as follows:

$$NMSE = \frac{\|x_{AA} - \tilde{x}_{AA}\|_2^2}{\|x_{AA}\|_2^2} \quad \text{Formula 6}$$

where $x_{AA}$ represents the simulated atrial fibrillation signal and $\tilde{x}_{AA}$ represents the atrial fibrillation signal extracted by an algorithm. The value of NMSE can be used to determine the similarity between the two signals.

In the experiment of extracting f wave, a real atrial fibrillation signal is taken from MIT-BIH atrial fibrillation signal database. An unnormalized ventricular residual (UVR) is used as the evaluation index.

$$uVR = \sqrt{\frac{\sum_{n=1}^{N_{QRS}} \tilde{x}_{AA}(n)^2}{N_{QRS}}} \cdot \max_{n=1,2,\ldots N_{QRS}} |\tilde{x}_{AA}(n)| \qquad \text{Formula 7}$$

Specifically, $N_{QRS}$ represents a length of QRS wave interval. All extracted atrial fibrillation signals have residual components of ventricular signals, so the lower the uVR, the better the extraction effect of the algorithm is.

In an experiment of simulating atrial fibrillation signal, the average NMSE of triple cross-validation is used to measure the performance of f wave extraction by different methods. In addition, through all the simulated atrial fibrillation signals to train the model parameters, the real atrial fibrillation signals are used for f wave detection and uVR is calculated, and finally the performance of f wave extraction is measured.

The experimental results described in Table 1 are obtained by triple cross-validation of simulated atrial fibrillation ECG data. The experimental results described in Table 2 are that all simulated atrial fibrillation ECG data are used to train the model.

TABLE 1

Signal extraction results of simulated atrial fibrillation

| Method | NMSE |
|---|---|
| DD-NLEM | 12.44 ± 30.99 |
| EKS | 120.76 ± 352.06 |
| DT-FENet w/o constrain | 0.24 ± 0.92 |
| DT-FENet | 0.22 ± 0.77 |

TABLE 2

Real atrial fibrillation signal extraction results

| Method | uVR ($10^{-3}$ mV$^2$) |
|---|---|
| DD-NLEM | 23.55 ± 28.63 |
| EKS | 147.76 ± 143.85 |
| DT-FENet w/o constrain | 10.51 ± 10.01 |
| DT-FENet | 8.41 ± 8.35 |

The results of simulation and real atrial fibrillation signal extraction experiments show that the single-lead f wave extraction method based on the two-channel temporal convolutional network can extract a cleaner f wave from ECG signals and has higher robustness.

The above embodiments are merely used to illustrate the technical scheme of the invention, but not to limit it; although the application has been described in detail with reference to the aforementioned embodiments, those of ordinary skill in the art should understand that the technical solutions described in the aforementioned embodiments can still be modified, or some of the technical features can be equivalently replaced; however, these modifications or substitutions do not make the essence of the corresponding technical solutions deviate from the spirit and scope of the technical solutions of each embodiment of the invention, and should be included in the protection scope of the invention.

What is claimed is:

1. A single-lead f wave extraction method, comprising:
establishing a two-channel temporal convolutional neural network model, wherein the two-channel temporal convolutional neural network model comprises two coding submodules, two mask estimation submodules, an information fusion module and two decoding submodules;

constructing a training data set of electrocardiography (ECG) signals, training the two-channel temporal convolutional neural network model according to the training data set of ECG signals to obtain a trained model, and saving the trained model; and extracting a reconstructed time domain signal of an f wave by inputting a measured mixed ECG signal into the trained model;

wherein the two coding submodules are respectively configured to extract a coding feature vector of a ventricular QRST complex and a coding feature vector of the f wave from the measured mixed ECG signal; the two mask estimation submodules are respectively configured to extract a potential feature vector of the f wave and a potential feature vector of the ventricular QRST complex according to the coding feature vector of the ventricular QRST complex and the coding feature vector of the f wave; the information fusion module is configured to perform feature fusion on the potential feature vector of the f wave and the potential feature vector of the ventricular QRST complex in a coding space, to estimate a mask feature vector of the ventricular QRST complex and a mask feature vector of the f wave; and the two decoding submodules are respectively configured to reconstruct a time domain signal of the ventricular QRST complex and a time domain signal of the f wave according to a weighted result of the mask feature vector and the coding feature vector of the ventricular QRST complex and a weighted result of the mask feature vector and the coding feature vector of the f wave to obtain a reconstructed time domain signal of the ventricular QRST complex and the reconstructed time domain signal of the f wave;

wherein the two-channel temporal convolutional neural network model is established based on a probability graph model, and the probability graph model is formulated by a probability factorization formula expressed as follows:

$$P(x_{VA}, x_{AA} | x) = \int_x P(x_{VA} | \tilde{Z}_{VA}) P(x_{AA} | \tilde{Z}_{AA}) P(\tilde{Z}_{VA} | M_{VA}, Z_{VA}) \cdot$$
$$P(\tilde{Z}_{AA} | M_{AA}, Z_{AA}) P(M_{VA} | F_{VA}, F_{AA}) P(M_{AA} | F_{VA}, F_{AA}) \cdot$$
$$P(F_{VA} | Z_{VA}) P(F_{AA} | Z_{AA}) P(Z_{VA} | x) P(Z_{AA} | x) dx$$

wherein $P(x_{VA}, x_{AA}|x)$ represents a conditional distribution probability being decomposed in the probability factorization formula, x represents the measured mixed ECG signal, $X_{VA}$ represents the reconstructed time domain signal of the ventricular QRST complex, $X_{AA}$ represents the reconstructed time domain signal of the f wave, $Z_{VA}$ and $Z_{AA}$ respectively represent the coding feature vectors of the ventricular QRST complex and the f wave, $F_{AA}$ and $F_{VA}$ respectively represent the potential feature vectors of the ventricular QRST complex and the f wave, $M_{VA}$ and $M_{AA}$ represent the mask feature vectors of the ventricular QRST complex and the f wave, $\tilde{Z}_{VA}$ and $\tilde{Z}_{AA}$ represent weighted feature vectors, and P ( ) represents a probability.

2. The method according to claim 1, wherein the constructing the training data set of the ECG signals comprises:

constructing the training data set $D_{tr}$ using a ECG signal data set marked with a QRST complex position and an f wave position, wherein $D_{tr}=\{x^i, x_{VA}, x_{AA}\}_{i=1}^{n_{tr}}$, $n_{tr}$ represents a total number of ECG records in the training data set, $x^i \in R^{1 \times T}$ represents an i-th ECG record of the ECG records, T represents the number of time sampling points, $x_{VA}^i \in R^{1 \times T}$ represents a clean QRST complex position label in the i-th ECG record, and $x_{AA}^i \in R^{1 \times T}$ represents a clean f wave position label in the i-th ECG record.

3. The method according to claim 1, wherein for each of the two coding submodules, a one-dimensional convolutional neural network is configured for coding, and the process of extracting the features of the ventricular QRST complex and the features of the f wave respectively by the two coding submodules comprises:
dividing each ECG record into K numbers of ECG segments each of a fixed length L, recorded as: $X \in R^{K \times L}$, where K is a positive integer;
inputting respectively X into the one-dimensional convolutional networks for the two coding submodules, to extract coding feature vectors of the ventricular QRST complex and the f wave, respectively recorded as $Z_{VA}$ and $Z_{AA} \in R^{K \times N}$, wherein N is the number of coding bases, and the coding feature vectors of the ventricular QRST complex and the f wave are calculated as follows:

$$\begin{cases} Z_{VA} = XB_{VA} \\ Z_{AA} = XB_{AA} \end{cases}$$

wherein $B_{VA}$ and $B_{AA} \in R^{L \times N}$ represent coding basis vectors.

4. The method according to claim 1, wherein the process of extracting the potential feature vector of the f wave and the potential feature vector of the ventricular QRST complex according to the coding feature vector of the ventricular QRST complex and the coding feature vector of the f wave by the two mask estimation submodules, comprises:
inputting the coding feature vectors $Z_{VA}$ and $Z_{AA}$ respectively into the two mask estimation submodules, to obtain the potential feature vectors of the f wave and the ventricular QRST complex, recorded as $F_{AA}$, $F_{VA} \in R^{K \times N}$, wherein each of the two mask estimation submodules uses a temporal convolutional network (TCN).

5. The method according to claim 1, wherein the process of performing by the information fusion module the feature fusion on the potential feature vector of the f wave and the potential feature vector of the ventricular QRST complex in the coding space to estimate the mask feature vector of the ventricular QRST complex and the mask feature vector of the f wave, comprises:
concatenating the potential feature vectors $F_{AA}$ and $F_{VA}$ in the coding space, to obtain a concatenated feature vector $F_{concat}=[F_{VA}, F_{AA}] \in R^{K \times 2N}$; and
inputting the concatenated feature vector into a one-dimensional convolution network, to estimate the mask feature vectors of the ventricular QRST complex and the f wave, respectively recorded as $M_{VA}$, $M_{AA} \in R^{K \times N}$.

6. The method according to claim 1, wherein obtaining the weighted result of the mask feature vector and the coding feature vector of the ventricular QRST complex and the weighted result of the mask feature vector and the coding feature vector of the f wave comprises:

weighting the mask feature vectors $M_{VA}$ and $M_{AA}$ output by the two mask estimation submodules respectively using the coding feature vectors $Z_{VA}$ and $Z_{AA}$, to obtain weighted feature vectors of the ventricular QRST complex and the f wave, respectively recorded as $\tilde{Z}_{VA}$, $\tilde{Z}_{AA} \in R^{K \times N}$, wherein the weighted feature vectors of the ventricular QRST complex and the f wave are calculated as follows:

$$\begin{cases} \tilde{Z}_{VA} = M_{VA} \odot Z_{VA} \\ \tilde{Z}_{AA} = M_{AA} \odot Z_{AA} \end{cases}$$

wherein $\odot$ represents a dot product of elements.

7. The method according to claim 1, wherein the process of reconstructing by the two decoding submodules the time domain signal of the ventricular QRST complex and the time domain signal of the f wave comprises:
inputting individually the weighted feature vectors $\tilde{Z}_{VA}$ and $\tilde{Z}_{AA}$ into a one-dimensional deconvolution network, to reconstruct the time domain signal of the ventricular QRST complex recorded as $\tilde{X}_{VA} \in R^{K \times L}$, and the time domain signal of the f wave recorded as $\tilde{X}_{AA} \in R^{K \times L}$, wherein the time domain signal of the ventricular QRST complex and the time domain signal of the f wave are calculated as follows:

$$\begin{cases} \tilde{X}_{VA} = \tilde{Z}_{VA} D_{VA} \\ \tilde{X}_{AA} = \tilde{Z}_{AA} D_{AA} \end{cases}$$

wherein $D_{VA}$, $D_{AA} \in R^{N \times L}$ represent decoding basis vectors; and
connecting K numbers of pieces of reconstructed fragments each of a length L $\tilde{X}_{VA}$ and $\tilde{X}_{AA}$ in series in turn, and estimating the time domain signals of the QRST complex and the f wave, recorded as $\tilde{x}_{VA}$, $\tilde{x}_{AA} \in R^{1 \times T}$, where K is a positive integer.

8. The method according to claim 1, wherein the two-channel temporal convolutional neural network model is trained using an objective function, expressed as follows:

$$\min J(\omega) = -\sum_{i=1}^{n_{tr}} SNR_{AA}^i - \alpha \cdot \sum_{i=1}^{n_{tr}} SNR_{VA}^i + \beta \cdot S_{VA};$$

wherein $\omega$ represents all trainable parameters of the two-channel temporal convolutional neural network model, $\alpha$ and $\beta$ represents compromise coefficients, $SNR_{VA}$ and $SNR_{AA}$ respectively represent a signal-to-noise ratio of the ventricular QRST complex and a signal-to-noise ratio of the f wave estimated by the model, $S_{VA}$ represents a sum of distances between the coding feature vectors of ventricular QRST complexes of every two of ECG samples, i represents a number of the i-th sample of the ECG samples, and $n_{tr}$ represents a total number of ECG records in the training data set.

9. A non-transitory computer readable storage medium, comprising a computer program, wherein when the computer program is executed by a processor, the steps of the method according to claim 1 are realized.

* * * * *